United States Patent [19]

Seelich

[11] Patent Number: 5,610,147
[45] Date of Patent: Mar. 11, 1997

[54] VIRUS-SAFE BLOOD COAGULATION FACTOR XIII PREPARATION

[75] Inventor: Thomas Seelich, Vienna, Austria

[73] Assignee: Immuno Aktiengesellschaft, Vienna, Austria

[21] Appl. No.: 280,514

[22] Filed: Jul. 26, 1994

[30] Foreign Application Priority Data

Aug. 3, 1993 [AT] Austria ..................... 1548/93

[51] Int. Cl.⁶ .................. A61K 38/36; A61K 35/16; C07K 14/745; C07K 14/47
[52] U.S. Cl. ................. 514/21; 514/8; 514/12; 530/380; 530/381; 530/427; 530/830
[58] Field of Search ................. 514/8, 12, 21; 530/380, 381, 383, 829, 830, 418, 427; 435/236, 238; 422/28, 29, 30, 31, 32, 33, 34, 36

[56] References Cited

U.S. PATENT DOCUMENTS

| | | | |
|---|---|---|---|
| 4,816,251 | 3/1989 | Seelich | 530/382 |
| 5,151,499 | 9/1992 | Kameyama et al. | 530/381 |
| 5,410,022 | 4/1995 | Eibl | 530/383 |

FOREIGN PATENT DOCUMENTS

| | | |
|---|---|---|
| 376883 | 1/1985 | Austria. |
| 0018561 | 11/1980 | European Pat. Off.. |
| 0037078 | 10/1981 | European Pat. Off.. |
| 0159311 | 10/1985 | European Pat. Off.. |
| 0519901 | 12/1992 | European Pat. Off.. |
| 80960 | 3/1988 | Japan. |

OTHER PUBLICATIONS

Mauler et al., "Inaktivierung von Viren in Faktor–XIII–Konzentrat durch Erhitzen in Losung", Arzneim.Forsch./Drug Res., 34, Table 2, (1984), pp. 1524–1527.
"Ad Hoc Working Party on Biotechnology/Pharmacy, Directive EC III/8115/89–EN of the Commission of the EC", pp. 1–15.
*Method for heating blood coagulation factor XIII*, Derwent Accession, No. 91–175118.

*Primary Examiner*—Mindy Fleisher
*Assistant Examiner*—Nancy J. Degen
*Attorney, Agent, or Firm*—Foley & Lardner

[57] ABSTRACT

The present invention relates to a virus-safe blood coagulation factor XIII preparation, which is obtained by heating an aqueous solution containing the blood coagulation factor XIII having a specific activity of at least 2 U/mg of total protein, wherein the solution containing less than 10% of known stabilizers selected from the group consisting of sugars, polyols, amino acids, peptides and carboxylic acids, as well as less than 0.5 mol ammonium sulfate per liter, wherein the heating is effected for a period of time sufficient to inactivate infectious agents, preferably for a period of time of from 30 min to 100 h.

20 Claims, No Drawings

VIRUS-SAFE BLOOD COAGULATION FACTOR XIII PREPARATION

The invention relates to a virus-safe blood coagulation factor XIII preparation of human origin bearing a low risk of infection and simultaneously having a high activity.

The pro-enzyme factor XIII is present in the blood plasma in the form of a- and b-chains ($a_2b_2$, molecular weight approximately 320,000 Da). Factor XIII of the formula $a_2$ (molecular weight approximately 160,000 Da), e.g., is found in placentas and thrombocytes. In both variants of factor XIII, the a-chains constitute the pro-enzyme proper, from which the active enzyme, factor XIIIa, is formed under the action of thrombin in the presence of $Ca^{2+}$ ions.

Factor XIII plays an essential role in the final phase of blood coagulation: simultaneously with the conversion of fibrinogen to fibrin (coagulation) caused by thrombin, factor XIII is activated to factor XIIIa in the presence of $Ca^{2+}$ ions, which factor XIIIa in turn covalently cross-links the fibrin monomers formed. The high polymer formed in this manner exhibits a substantially higher mechanical strength than non-cross-linked fibrin and also is more resistant to fibrinolytic degradation, which is of decisive importance for effectively stopping bleedings. Moreover, the presence of factor XIII is a necessary pre-requisite for normal wound healing.

When being injured, factor XIII-deficient patients suffer from severe disturbances in the stoppage of bleedings and healing of wounds, which can only be eliminated by intravenous administration of factor XIII preparations. Yet also in tissue adhesives based on fibrinogen and factor XIII ("fibrin adhesive"), a sufficient content of factor XIII is essential to obtain the desired high strength of the adhesions, and effective stoppage of bleedings and good wound healing.

Finally, there is a demand for standardized factor XIII preparations for medical-diagnostical purposes.

Factor XIII preparations, in particular those to be administered to a human, are obtained from human plasma and from human placentas. Due to the starting material used, basically there exists the risk of transmitting infectious agents, such as viruses, which cannot be removed by sterile filtration.

For all the applications mentioned there is the demand that the factor XIII preparations practically must not bear any risk of infection, so as to put neither patients nor the staff at risk. This requirement is particularly important with preparations to be administered to a human, and is of the utmost importance with infusion preparations which must be administered, e.g. to factor XIII-deficient patients, throughout their lives at regular intervals. For with all preparations which are not absolutely free from infectious particles, this repeated administration would lead to an accumulation of these particles in the patient and thus to a substantially increased risk of infection.

Thus it has been attempted to minimize this risk as far as possible, i.e. by testing the starting material, on the one hand, and by additional measures for inactivating any infectious agents possibly present, on the other hand. The starting material can, however, only be tested for infectious agents already known and for which also suitable testing methods are available (hepatitis and HI viruses); yet it is not possible to test for other, unknown infectious agents that may be present. Moreover, the sensitivity of all the testing methods is limited, so that already for this reason no absolute safety can be expected.

All the methods of inactivating pathogens, such as viruses, in labile biological preparations have the basic problem that the method should reduce the virus titer as much as possible, on the one hand, while reducing the biological activity to the least possible extent, on the other hand.

Today, virus inactivation methods are called effective if after application of the method on a test preparation which had been admixed with a high dose of a test virus (e.g. corresponding to a maximum possible titer of approximately $10^{5.5}$ ID/ml in a coagulation factor preparation), no viruses can be detected any longer in the sample and the virus titer thus has been reduced to below the detection limit.

As a validation of inactivation, the so-called "reduction factor" ("virus reduction factor") is known, which, after a single addition of test virus, is calculated from the decadic logarithm of the quotient of the initial and final virus titers. From the directive EC III/8115/898-EN of the Commission of the European Communities, furthermore the so-called total reduction factor is known. It is calculated from the sum of the reduction factors of individual subsequent inactivation measures.

Thus, the ratio of reduction factor (RI) or total reduction factor (R) to the biological residual activity (RA) after carrying out of the method serves to validate virus inactivation methods.

There are already known methods of inactivating pathogens in factor XIII preparations by heating in solution (pasteurizing) (EP-A-0 018 561, EP-A-0 037 078). The biological activity of factor XIII can be substantially retained by the addition of known stabilizers, such as amino acids, peptides, sugars, polyols or carboxylic acids, so-called "thermostabilizers", which must be used in an amount of more than 10% to 50% (sirup method). Furthermore, human albumin at a concentration of more than 0.1% has been suggested as a thermo-stabilizer (JP 80960/1988). Also a method of stabilizing blood coagulation factors by the addition of more than 0.5 M ammonium sulfate prior to a heat treatment is known (AT 376 883).

However, the necessary removal of the highly concentrated thermo-stabilizers from the heated products is cumbersome. Virus inactivation methods by pasteurizing in the presence of stabilizers furthermore have the disadvantage that simultaneously with the desired biological activity, also the viruses themselves are stabilized, thus not yielding a particularly favorable ratio of reduction factor to residual activity (R/RA).

Hitherto, the liquid heating of factor XIII-containing solutions without stabilizers appeared impossible from the expert point of view; thus, in a comparative example in EP-A-0 037 078, factor XIII was heated for 10 hours at 60° C. without the addition of stabilizers. In doing so, the activity of factor XIII was completely destroyed.

The invention has as its object to provide a virus-safe blood coagulation factor XIII preparation, from which it can be expected that the transmission of infectious agents is excluded even if large amounts of factor XIII are administered, and which has a high activity nevertheless. The invention furthermore has as its object to provide a method of inactivating infectious agents in a factor XIII-containing preparation by heating in solution, which does not exhibit the disadvantages inherent in the known pasteurizing methods.

According to the invention, these objects are achieved by a virus-safe blood coagulation factor XIII preparation, which is obtainable by heating an aqueous solution containing the blood coagulation factor XIII with a specific acitivity of at least 2 U/mg total protein, which solution contains less than 10% of known stabilizers selected from the group consisting of sugars, polyols, amino acids, peptides and carboxylic acids, as well as less than 0.5 mol of ammonium sulfate per liter, wherein heating is effected for a period of time sufficient to inactivate infectious agents, preferably for 30 min to 100 h.

The invention further comprises a method of producing a virus-safe blood coagulation factor XIII preparation, wherein infectious agents are inactivated by heating, and which is characterised in that an aqueous solution of a factor XIII-containing fraction which contains less than 10% of known stabilizers selected from the group consisting of sugars, polyols, amino acids, peptides and carboxylic acids, as well as less than 0.5 mol of ammonium sulfate per liter, and has a specific activity of at least 2, preferably at least 15, units/mg of total protein, at a temperature of from 40° to 65° C. for a period of time sufficient to inactivate infectious agents, preferably for 30 min to 100 h.

Surprisingly, it has been found that when heating factor XIII-containing solutions in the absence of or at a low content of known stabilizers, an extremely favorable, hitherto unattained ratio of virus reduction factor to factor XIII residual activity is obtained. Comparative assays have shown that a certain reduction of the HIV titer by heating in solution (60° C.) requires heating periods that are longer by at least ten times, if heating is effected in the presence of stabilizers (50% sucrose, 2 M glycine in accordance with EP-A-0 018 561).

The fact that the factor XIII activity was preserved to the major extent was the more surprising, since factor XIII is considered to be relatively heat-labile, when the latter is, e.g., subjected to a heat treatment according to EP-B-0 159 311.

The method according to the invention is effected at a temperature and for a period of time at which more than 50% of the biologic activity of factor XIII is preserved.

A preferred embodiment of the method is characterised by the following measures:

providing a factor XIII-containing COHN I-fraction, precipitating factor XIII from the COHN I-fraction and separating the precipitate, if desired, further purifying the factor XIII-containing precipitate by dissolving and reprecipitating, short-term heating the dissolved precipitate and separating heat-denatured fibrinogen, if desired, further purifying and concentrating the factor XIII-containing solution, heating the factor XIII-containing solution without the addition of known stabilizers at a temperature of from 40° to 60° C. for a period of time of from 30 min to 2 h.

Precipitation of factor XIII from the dissolved COHN I-fraction may, e.g., be effected with ammonium sulfate (approximately 10 to 20% saturation at 20° C.) or with glycine (approximately 1.5 to 3 mol/l). Also other precipitating agents which are known to be suitable for precipitating factor XIII (in the presence of fibrinogen) may be used.

After separation and dissolution of the precipitate obtained, precipitation may be repeated with the same or with a different precipitating agent. The precipitate is then dissolved and heated for a short time (e.g. 3 min at 56° C.) to denature and precipitate any fibrinogen present. The supernatant obtained after the heat precipitation has a total protein content of approximately 0.5 to 2.5 mg/ml and contains factor XIII which has a specific activity of from approximately 2 to 10 U/mg total protein.

This factor XIII-containing solution may be further purified in that accompanying proteins are precipitated and separated by the addition of polyethylene glycol (e.g. PEG 4000 up to a concentration of approximately 3.5% at approximately 4° C.).

Thereupon, factor XIII may be precipitated by the addition of PEG 4000 up to a concentration of 10% and dissolved in a buffer solution, e.g. a 0.1% citrate solution, pH 7.0, to a concentration of several hundred units per ml.

The solution thus obtained is then heated without the addition of known stabilizers (e.g. at 60° C. for 2 hours, or at 50° C. for 12 hours), the factor XIII activity being substantially preserved.

In a preferred embodiment, the solution to be heated additionally contains a tenside, preferably a non-ionic tenside. The tenside concentration is to be selected variably, depending on the type of tenside used. A concentration at which the tenside additionally is virucidically active during the heating procedure, yet the factor XIII activity is not substantially impaired, is suitable.

Such a suitable concentration may be determined for each desired tenside by way of experiment in a simple manner.

Suitable concentrations, e.g., for desoxycholate, are below 0.2% (w/v), for benzyl trimethyl ammonium chloride and benzyl-dimethyl-2-hydroxyethyl-ammonium-chloride are below 0.1% (w/v), for sulfobetaine SB 12 (of Serva; N-dodecyl-N',N-dimethylammonio-1-propanesulfonate) are below 0.3% (w/v), and for N-octyl glucoside are below 1% (w/v), while tensides such as Tween 80 or Triton X-100 may also be used at substantially higher concentrations [15% (w/v) and thereabove].

Surprisingly, it has been shown that the stability of factor XIII when heated in solution in the presence of tensides, approximately is just as good as in the absence thereof, whereas virus inactivation proceeds even more rapidly, so that on the whole an even more favorable ratio of virus reduction factor to factor XIII residual activity is obtained. If necessary, the tenside added may be removed again after the heating step by methods known per se, such as, e.g., reprecipitation or ion exchange chromatography.

On account of its hitherto unattained safety in respect of the transmission of infectious agents, such as heptatitis or AIDS viruses (HIV) with simultaneous high specific enzyme activity, the preparation according to the invention is suited for the production of preparations for the prophylactic and therapeutic administration to a human, for the production of tissue adhesives as well as for diagnostic purposes.

A preferred application of the virus-safe blood coagulation factor XIII preparation consists in the production of a virus-safe tissue adhesive preparation by addition of the factor XIII to an already virusin-activated fibrinogen preparation.

The duration of the heat treatment according to the invention for obtaining the desired reduction factor may be determined experimentally on a factor XIII sample to which a certain amount of test virus has been admixed.

For virus inactivation, the factor XIII sample is heat treated at a certain temperature, until a virus titer that is still measurable has been obtained. From the reduction of the virus titer per time unit it is possible to calculate the time of treatment which is necessary to obtain a desired total reduction of the virus titer.

When calculating in this manner, it is presupposed that the virus inactivation is a reaction of the first order with unchanging rate constant.

Even if this is not always the case in practice, yet a reduction of the efficacy of a method is frequently observed during its time course (so-called tailing), the manner of calculating described still is an acknowledged method of comparing the efficacy of various virus inactivation methods with one another.

It is, however, also possible according to the method of EP 0 519 901 to repeatedly add definite amounts of test virus during the heat treatment, each repetition being made only if the virus titer has sunk to a certain value, preferably to below the detection limit. The total reduction factor then results from the sum of the individual reduction factors.

It turned out that for carrying out the method of the invention, a fraction containing highly purified factor XIII is particularly suitable. Accordingly, a preferred embodiment of the method of the invention consists in that, prior to heat inactivation, the factor XIII-containing fraction is purified and, if desired, concentrated so as to obtain a specific activity of factor XIII of at least 15 units per mg of total protein.

It was surprising that when carrying out the method of the invention, the stability of factor XIII is the higher, the more the preparation has been purified, i.e. the higher its specific activity.

Quite the opposite would have to be expected, since generally, labile enzymes are stabilized by the presence of other proteins (a known example is albumin).

Surprisingly, it has been found, however, that in the method according to the invention, albumin has no stabilizing effect on factor XIII and that also other plasma proteins do not act as stabilizers, either.

It is advantageous to obtain the factor XIII-containing fraction from plasma. Factor XIII then will comprise both, a-chains and b-chains.

It is advantageous to separate fibrinogen possibly present prior to carrying out the method according to the invention. In the presence of heat-denatured fibrinogen, inclusions of viruses could also occur. Such enclosed viruses could be stabilized relative to heat action and thus make the reliability of the method questionable. After heating for a short time (e.g. at 56° C. to 60° C. for a few minutes), fibrinogen is denatured and can then be separated as a precipitate.

The method according to the invention may be carried out at any stage of the plasma fractionation method at which factor XIII is present in solution with a specific activity of at least 2 units per mg of total protein.

In the following Examples, the following analytical methods have been applied:

Total protein: Biuret method

Factor XIII: The determination was effected according to two different methods, which, however, both are based on the same basic principle, i.e. the cross-linking of fibrin by factor XIII.

Method 1:

Aliquots of a fibrinogen solution free from factor XIII are mixed with different dilutions of the sample to be determined and a thrombin-CaCl$_2$-solution and incubated at 37° C. After a certain incubation time, the reaction is stopped by the addition of 1% monochloroacetic acid (MCA), and the solubility or insolubility of the fibrin clots in MCA is determined.

Pooled, deep frozen human citrated plasma serves as the standard, wherein, by definition, 1 ml of plasma contains 1 unit of factor XIII.

The highest dilutions of sample and standard, respectively, by which insoluble clots are still obtained serve to calculate the factor XIII content of the unknown sample (x) according to the formula $$x = \frac{Vx}{Vs}, \text{ wherein}$$

Vx is the dilution of the unknown sample and Vs is the dilution of the standard.

This common determination method thus is finally based on the solubility of non-cross-linked or the insolubility of cross-linked fibrin in 1% monochloroacetic acid. Its precision therefore is limited by the inexactness of this solubility limit.

Method 2:

The reaction mixtures correspond to those of method 1, yet the reaction is stopped by the addition of a mixture of urea, Na-dodecyl sulfate (SDS) and β-mercapto-ethanol, and the disulfide bridges contained in the proteins are split by reduction.

The degree of cross-linking of the fibrin-γ-chains in the samples thus obtained is densitometrically determined after SDS gel electrophoresis and staining with Coomassie Blue. By graphic interpolation, those dilutions of sample and standard are obtained therefrom, at which the cross-linking of the fibrin-δ-chains amounts to 50%. If these dilutions are Vx and Vs, respectively, the factor XIII content of the unknown sample (x) is calculated as in method 1 according to the formula $$x = \frac{Vx}{Vs}.$$

By its nature, method 2 is more precise than the (common) method 1, yet it also involves much more work.

Method 2 thus was used if a higher precision of the factor XIII determination seemed advantageous or necessary for describing the method of the invention.

EXAMPLE 1:

Production of a factor XIII solution free from fibrinogen (heat precipitation supernatant)

A conventional COHN I precipitate (obtained from a plasma fraction containing fibrinogen and factor XIII by precipitation with ethanol) was dissolved with a 10-fold amount of a citrate-containing buffer solution, pH 7.0 (0.05 M citrate, 0.5 M NaCl, 20.000 KIU aprotinin/l) and admixed with ammonium sulfate under stirring up to a 16% saturation (at room temperature). Thereupon it was cooled to 4° C., and the mixture was stirred for another 2 hours. The precipitate formed was dissolved with the buffer solution described, and precipitation was repeated once with ammonium sulfate.

The precipitate was dissolved in a citrate-containing buffer solution, pH 7.0 (0.02 M citrate-containing 0.12 M NaCl, 100 KIU aprotinin/ml) and heated to 56° C. for 10 minutes. The precipitate formed (from denatured fibrinogen) was centrifuged off. The heat precipitation supernatant had a protein content of 2.1 mg/ml and a factor XIII content (according to Method 2) of 7.7 U/ml. The specific activity thus was 3.7 U of factor XIII/mg of protein.

EXAMPLE 2:

Stability of factor XIII when heating the solution

Heat precipitation supernatants corresponding to Example 1 were heated at temperatures of from 40° to 65° C. without the addition of stabilizers. After a certain duration of the heat treatment, the residual activity of factor XIII, based on the activity prior to heating, was determined.

TABLE 1

Heating of heat precipitation supernatant without the addition of stabilizers

| Temp. | duration (h) | resid. activity(%) | determined acc. to method |
|---|---|---|---|
| 40° C. | 7 | 100 | 1 |
| | 24 | 80 | 1 |
| 50° C. | 7 | 100 | 1 |
| | 24 | 80 | 1 |
| 60° C. | 1 | 85 | 2 |
| | 2 | 73 | 2 |
| | 4 | 50 | 2 |
| 65° C. | 0.5 min | 85 | 1 |
| | 1 min | 75 | 1 |
| | 2 min | 55 | 1 |

EXAMPLE 3:

Specific activity and stability of factor XIII when heating in solution

The stability of the following factor XIII solutions when heated in solution without stabilizers was compared:

A) The heat precipitation supernatant of Example 1

B) For further purification, the ammonium sulfate precipitate of Example 1 was dissolved in a citrate-containing buffer solution (0.02 M citrate, 0.12 M NaCl, 50,000 KIU aprotinin/l) and reprecipitated with glycine (1.75 mol/l). The precipitate was dissolved in the same buffer solution, and the heat precipitation was carried out according to Example 1.

C) A heat precipitation supernatant according to Example 1 was further treated in the following manner for further purification and concentration:

1) Separation of accompanying proteins by precipitation with 3.5% (w/v) PEG 4000 at 4° C.

2) Total precipitation of factor XIII from the supernatant by the addition of PEG 4000 up to a concentration of 10% (w/v) at 4° C., separation of the precipitate by centrifugation and dissolving in 1/25 of the original volume of a 0.1% Na citrated buffer, pH 7.0.

The factor XIII residual activity of the three solutions A, B, C after heat treatment (60° C. for 4 hours, without stabilizers) was determined (Method 2).

TABLE 2

Heating of factor XIII-containing solutions of varying purities

| Solution | specif. activity (U/mg total protein) | residual activity (%) after 4 h, 60° C. |
|---|---|---|
| A) | 3.7 | 50 |
| B) | 17 | 82 |
| C) | 35 | 95 |

The Example shows that the stability of factor XIII increases with its purity (specific activity) when heated in solution without stabilizers.

EXAMPLE 4:

Stability of factor XIII when heating in solution (without stabilizers) in the presence of a tenside A factor XIII-containing solution was produced according to Example 3, Variant C. The specific activity amounted to 21 U factor XIII/mg protein. The solution was divided, and one part was admixed with 1% (w/v) Tween 80. Both solutions were heated at 60° C. for 6 hours. After heating for 6 hours, the factor XIII residual activities amounted to 82% without the addition of a tenside, and to 84% with the addition of a tenside (determined according to Method 2).

EXAMPLE 5:

Example 4 was repeated with various tensides in varying concentrations (heating: 4 h, 60° C.).

TABLE 3

Heating of a factor XIII-containing solution in the presence of a tenside

| Tenside | Concentration % (w/v) | FXIII-resid. activity % |
|---|---|---|
| Tween 80 | 15 | 97 |
| Triton X-100 | 15 | 91 |
| Pluronic P 85 | 10 | 96 |
| N-Octylglucoside | 0.3 | 86 |
| Na-Desoxycholate | 0.1 | 67 |
| Benzyl-trimethyl ammonium-chloride | 0.01 | 97 |
| Benzyl-dimethyl-2-hydroxyethyl-ammonium chloride | 0.01 | 93 |
| Sulfobetaine SB 12 | 0.03 | 93 |
| | 0.1 | 63 |

Examples 4 and 5 show that the method according to the invention can be carried out without any problems also in the presence of non-ionic, anionic, cationic or zwitter-ionic tensides, without having to put up with major losses of factor XIII activity.

The following Examples 6 and 7 demonstrate the efficacy of the method according to the invention.

EXAMPLE 6:

Inactivation of model viruses according to the method of the invention in the presence or absence of denatured fibrinogen.

Samples of factor XIII-containing fractions according to Example 1, either A) prior to heat precipitation and separation of the fibrionogen, or B) after separation of the heat precipitation precipitate were admixed with 10 vol.-% of suspensions of Sindbis, Vaccinia, Polio or Vesicular Stomatitis (VS) virus and heated at 60° C., the virus titer was determined after varying periods of heating, and the reduction factor (R), based on a heating period of 60 min, was calculated. In variant A) the virus titer determination was effected analogous to B) from the heat precipitation supernatants formed during heating.

The results are listed in Table 4.

TABLE 4

Reduction of virus titer in a factor XIII-
containing solution in the presence or absence
of denatured fibrinogen (Variant A or B,
respectively)

Virus titer (log10) after minutes at 60° C.

| Virus | Variant | 0 | 5 | 10 | 15 | 20 | 30 | 45 | 60 | R |
|---|---|---|---|---|---|---|---|---|---|---|
| Sindbis | A | 6.5 | — | ≦0.5 | — | ≦0.5 | ≦0.5 | ≦0.5 | ≦0.5 | ≧36 |
| Vaccinia | | 6.2 | — | 2.5 | — | 0.7 | ≦0.5 | ≦0.5 | ≦0.5 | 16.5 |
| Polio | | 7.0 | — | ≦0.5 | — | ≦0.5 | ≦0.5 | ≦0.5 | ≦0.5 | ≧39 |
| Sindbis | B | 6.5 | — | ≦0.5 | — | ≦0.5 | ≦0.5 | ≦0.5 | ≦0.5 | ≧36 |
| Sindbis | | 6.4 | 1.2 | ≦0.5 | ≦0.5 | — | ≦0.5 | — | ≦0.5 | 62 |
| Vaccinia | | 6.2 | — | 1.0 | — | ≦0.5 | ≦0.5 | ≦0.5 | ≦0.5 | 31.2 |
| Polio | | 7.0 | — | ≦0.5 | — | ≦0.5 | ≦0.5 | ≦0.5 | ≦0.5 | ≧39 |
| VSV | | 7.0 | 0.7 | ≦0.5 | ≦0.5 | — | ≦0.5 | — | ≦0.5 | 54 |

The results demonstrate the excellent efficacy of the method as compared to the known method most similar thereto, i.e. pasteurizing in the presence of stabilizers.

The efficacy of this known method is known e.g. from R. Mauler and J. Hilfenaus, Arzneim.Forsch./Drug Res. 34, 1524–1527, 1984, Table 2, p. 1526.

If one calculates the respective reduction factors (1 h, 60° C.) for Polio and Vaccinia viruses and determines (by graphic interpolation) those heating periods (60° C.), after which a virus titer reduction of $10^5$ occurs (R=5), there results the following comparison (Table 5):

TABLE 5

Comparison of virus inactivation capacities
of the method of the invention and of a
method of the prior art

| Method | Virus | R (1 h 60° C.) | Heating period 60° C. (R = 5) |
|---|---|---|---|
| Prior Art (Mauler et al) | Polio | 1.2 | 4 h 10 min |
| | Vaccinia | 1.75 | 2 h 52 min |
| Method acc. to the invention | Polio | ≧39 | <8 min |
| | Vaccinia | 31 | 10 min |

The results (Table 4) furthermore show by way of the example of the Vaccinia virus that it is advantageous to remove prepipitated denatured protein

EXAMPLE 7:

Inactivation of a model virus (Sindbis) according to the method of the invention in the presence or absence of a tenside A factor XIII-containing solution according to Example 3, Variant C, was divided, and one portion was admixed with 0.3% (w/v) N-Octylglucoside.

Both solutions were heated at 60° C., admixed with 10 vol.-% of a Sindbis virus suspension (start of the virus inactivation reaction) and further incubated at 60° C. At certain time intervals samples were drawn and the virus titer was determined.

The results are listed in the following Table 6.

TABLE 6

Virus inactivation in a factor XIII-containing
solution with and without tenside at 60° C.

| Duration of heating at 60° C. (minutes) | virus titer (log 10) | |
|---|---|---|
| | without tenside | with tenside |
| 0 | 8.1 | 8.1 |
| 0.5 | 5.75 | 1.88 |
| 1 | 5.0 | ≦1.5 |
| 1.5 | 4.25 | ≦1.5 |
| 2 | 3.88 | ≦1.5 |
| 2.5 | 3.75 | ≦1.5 |
| 3 | 3.25 | ≦1.5 |
| 3.5 | 2.75 | ≦1.5 |
| 4 | 2.63 | ≦1.5 |
| 4.5 | 2.5 | ≦1.5 |
| 5 | 2.38 | ≦1.5 |
| 6 | 1.88 | ≦1.5 |
| 7 | 2.1 | ≦1.5 |
| 8, 10, 15, 20, 30 | ≦1.5 | ≦1.5 |

The Example shows that the method of the invention is even more effective if carried out in the presence of a tenside:

An even faster and more extensive virus inactivation is attained without having to put up with major losses of factor XIII activity (cf. Example 5).

What I claim is:

1. A method for producing an aqueous pharmaceutical preparation comprising factor XIII, comprising the steps of:
    obtaining an aqueous solution comprising at least 2 U of factor XIII/mg protein, and
    heating said solution at 40° to 65° C. in order to inactivate viruses to form said virus-safe factor XIII preparation without adding thermostabilizers, wherein said aqueous pharmaceutical preparation has more than 50% of the original biological activity of the factor XIII present in said aqueous solution before said heating step.

2. A method as set forth in claim 1, wherein said heating is effected for a period of time of from 30 min to 100 h.

3. A method as set forth in claim 1, wherein said heating is effected in the presence of a tenside.

4. A method as set forth in claim 3, wherein said tenside is a non-ionic tenside.

5. A method as set forth in claim 1, wherein said solution is substantially free from known stabilizers.

6. A method according to claim 1, wherein said pharmaceutical preparation has at least 60% of the original biological activity of the factor XIII present in said aqueous solution before said heating step.

7. A method according to claim 6, wherein said pharmaceutical preparation has at least 70% of the original biological activity of the factor XIII present in said aqueous solution before said heating step.

8. A method according to claim 1, wherein said aqueous solution comprises at least 15 U of factor XIII/mg protein.

9. A virus-safe aqueous factor XIII preparation obtainable by heating an aqueous solution containing factor XIII having a specific activity of at least 2 U/mg of total protein to inactivate viruses, wherein said solution has a thermostabilizer content of less than 10% and an ammonium sulfate content of less than 0.5 mol per liter, wherein no thermostabilizers are added during said heating, and more than 50% of the original biological activity of the factor XIII is maintained in said virus-safe aqueous factor XIII preparation.

10. The virus-safe aqueous factor XIII preparation as set forth in claim 9, wherein said heating is effected in the presence of a tenside.

11. The virus-safe aqueous factor XIII preparation as set forth in claim 9, wherein said solution is substantially free from known stabilizers.

12. A method for producing an aqueous, virus-safe factor XIII preparation, comprising the steps of:
   (a) obtaining an aqueous COHN-I fraction comprising factor XIII;
   (b) precipitating said factor XIII from said COHN-I fraction to form a factor XIII containing precipitate and separating said factor XIII containing precipitate from the remainder of said COHN-I fraction;
   (c) dissolving said factor XIII containing precipitate in an aqueous buffer to form a factor XIII solution;
   (d) heating said factor XIII solution to denature fibrinogen in said solution and form an aqueous factor XIII supernatant;
   (e) removing the denatured fibrinogen from said aqueous factor XIII supernatant so that said supernatant comprises at least 2 U of factor XIII/mg protein;
   (f) heating said aqueous factor XIII supernatant at about 40° to 60° C. for about 0.5 hours to 2 hours without adding thermostabilizers in order to form said virus-safe factor XIII preparation, wherein said virus-safe factor XIII preparation has more than 50% of the original biological activity of the factor XIII present in said aqueous solution before said heating step.

13. A method according to claim 12, wherein a tenside is added during said heating step (f).

14. A method according to claim 13, wherein said tenside is a non-ionic tenside.

15. An aqueous, virus-safe tissue adhesive comprising a virus-safe factor XIII preparation obtainable by heating an aqueous solution containing factor XIII having a specific activity of at least 2 U/mg of total protein to inactivate viruses, wherein said solution has a thermostabilizer content of less than 10% and an ammonium sulfate content of less than 0.5 mol per liter, wherein no thermostabilizers are added during said heating, and more than 50% of the original biological activity of the factor XIII is maintained.

16. A tissue adhesive according to claim 15, further comprising virus-safe fibrinogen.

17. An aqueous, virus-safe therapeutic composition comprising a virus-safe factor XIII preparation obtainable by heating an aqueous solution containing factor XIII having a specific activity of at least 2 U/mg of total protein to inactivate viruses, wherein said solution has a thermostabilizer content of less than 10% and an ammonium sulfate content of less than 0.5 mol per liter, wherein no thermostabilizers are added during said heating, and more than 50% of the original biological activity of the factor XIII is maintained in said aqueous, virus-safe therapeutic composition.

18. An aqueous, virus-safe diagnostic assay comprising a virus-safe factor XIII preparation obtainable by heating an aqueous solution containing factor XIII having a specific activity of at least 2 U/mg of total protein to inactivate viruses, wherein said solution has a thermostabilizer content of less than 10% and an ammonium sulfate content of less than 0.5 mol per liter, wherein no thermostabilizers are added during said heating,. and more than 50% of the original biological activity of the factor XIII is maintained in said aqueous, virus-safe diagnostic assay.

19. An aqueous, virus-safe factor XIII preparation having a specific activity of at least 2 U/mg of total protein, wherein said preparation is stable and is substantially free of thermostabilizers.

20. An aqueous pharmaceutical preparation comprising factor XIII preparation having a specific activity of at least 2 U/mg of total protein, wherein said preparation is virus-safe, stable and is substantially free of thermostabilizers.

* * * * *

UNITED STATES PATENT AND TRADEMARK OFFICE
CERTIFICATE OF CORRECTION

PATENT NO. : 5,610,147
DATED : March 11, 1997
INVENTOR(S) : Thomas SEELICH

It is certified that error appears in the above-indentified patent and that said Letters Patent is hereby corrected as shown below:

On title page, insert the following: --[*] Notice: The term of this patent shall not extend beyond the expiration date of U.S. Patent No. 5,639,730 --.

Signed and Sealed this

Eleventh Day of August 1998

Attest:

BRUCE LEHMAN

*Attesting Officer*  *Commissioner of Patents and Trademarks*